United States Patent [19]

Khanna et al.

[11] Patent Number: 4,786,594
[45] Date of Patent: Nov. 22, 1988

[54] ENZYME IMMUNOASSAY

[75] Inventors: Pyare Khanna, San Jose; Dennis M. Bleile, Redwood City; Cynthia D. Stiso, Sunnyvale, all of Calif.

[73] Assignee: Syntex (U.S.A.) Inc., Palo Alto, Calif.

[21] Appl. No.: 863,268

[22] Filed: May 14, 1986

[51] Int. Cl.$^4$ .................. G01N 53/00; G01N 21/00; G01N 33/552
[52] U.S. Cl. .......................... 435/7; 422/56; 422/57; 422/58; 422/60; 422/61; 422/102; 435/175; 435/805; 435/810; 436/503; 436/525; 436/527; 436/530; 436/531; 436/823; 436/824
[58] Field of Search ...................... 422/56, 57, 58, 60, 422/61, 102; 435/7, 175, 805, 810; 436/503, 525, 527, 530, 531, 823, 824

[56] References Cited

U.S. PATENT DOCUMENTS

| | | | |
|---|---|---|---|
| 3,850,752 | 11/1974 | Schuurs et al. | 436/530 X |
| 4,105,415 | 8/1978 | Lovett | 422/58 |
| 4,299,916 | 11/1981 | Litman et al. | 435/805 X |
| 4,540,659 | 9/1985 | Litman et al. | 436/527 X |
| 4,596,768 | 6/1986 | Singh et al. | 436/530 X |

Primary Examiner—Robert J. Warden
Assistant Examiner—Richard Wagner
Attorney, Agent, or Firm—Theodore J. Leitereg

[57] ABSTRACT

A method is disclosed for determining an analyte in a sample suspected of containing the analyte. The analyte is a member of a specific binding pair (sbp) consisting of ligand and complementary receptor. The method comprises combining in an aqueous medium (1) said sample, (2) a first reagent comprising a non-dispersed surface to which is bound an sbp member that becomes bound to the surface in relation to the amount of analyte in the sample. The volume of the aqueous medium containing the above reagents is sufficiently large to allow complete immersion of the first reagent therein and determination of the analyte but not so large to result in substantial interference in the determination upon addition of a second reagent reactive with the conjugate of enzyme and sbp member and capable of generating a signal. The second reagent is present in a medium of sufficient volume to substantially increase the volume of the liquid medium and reduce interference in the determination. The second reagent is added to the first liquid medium without separation of the first reagent therefrom. The first reagent of the medium is examined for the presence of the signal. The present method avoids a separation and washing step normally found in separation assays. Thus, the present invention is less time consuming and less labor intensive. An apparatus for performing the above assay comprises a vessel having at least one vertical side wall, an open end and a single closed end generally opposite the open end. A discontinuously narrowed portion is adjacent the closed end and defines a well. A ledge depends from a vertical side wall adjacent the narrowed portion. Preferably, the vessel and the narrowed portion are cylindrical. A kit for performing the assay method of the invention is also described.

23 Claims, 1 Drawing Sheet

ENZYME IMMUNOASSAY

BACKGROUND OF THE INVENTION

1. Field of the Invention

There is a continuing interest in developing new, simpler and more rapid techniques to detect and measure the presence of an analyte in a sample. The analyte can be any of a wide variety of materials such as drugs, naturally occuring physiological compounds, pollutants, chemicals, contaminants, or the like. In many cases speed is important for the measurement, particularly with certain physiologically active compounds. In other situations, convenience and ease of operation can be major considerations.

In order to quantitate the amount of analyte present in an enzyme immunoassay, the extent of reaction of an enzyme-labelled ligand with antibody must be determined. In the case of heterogeneous enzyme immunoassays, this requires a physical separation of the free and antibody-bound fractions. In order to maximize precision and sensitivity, complete separation of the free and bound fractions should be accomplished with relatively simple and fool proof manipulations. The separation should be accomplished rapidly, preferably without elaborate or expensive equipment. Some configurations employed in enzyme immunoassays include an immobilized antigen, an immobilized antibody, a sandwich method, and/or a bridge or unlabelled antibody.

Exemplary of heterogeneous enzyme immunoassays is the enzyme-linked immunosorbent assay (ELISA). ELISA includes a separation of enzyme-labelled antigen-antibody complex (bound enzyme) from free enzyme-labelled antigen or antibody. The enzymatic activity in the bound or free fraction is quantitated by the enzyme-catalysed conversion of a relatively non-chromatic or nonfluorescent substrate to a highly chromatic or fluorescent product. The various ELISA assay techniques have been classified as either competitive or noncompetitive depending on whether the technique involves a reaction step in which unlabelled antigen and antigen linked to an enzyme or attached to a solid phase compete for a limited number of antibody binding sites, or whether the antigen or antibody to be measured is allowed to react alone with an excess of immune reactant. Whether the approach is competitive or noncompetitive, the ELISA technique involves at least one, and more than likely at least two or three, separation and wash steps. First, there is generally a separation and a wash step after the attachment of antigen or antibody to a solid phase. Secondly, there is a separation and a wash step after incubation of enzyme-labelled antibody. Additionally, in noncompetitive ELISA there is an additional separation and wash step.

In the case of homogenous enzyme immunoassays, no separation of the enzyme labeled antigen-antibody complex from the free enzyme labeled antigen or antibody is required. The enzyme activity of the bond or free fraction can be determined without separation because the enzyme activity changes as a result of binding. Because no separation is employed, these assays frequently are adversely affected by the sample medium and thus only relatively small amounts of sample can be used in the assay medium and the assay sensitivity is thereby reduced. Moreover, it is usually not possible to use excess enzyme labeled reagents because the modulator of the activity of the bound reagent would not be measurable with a large background signal. For these reasons it is sometimes desirable to bind one of the reagents on a solid surface that can be contacted with the sample and/or the enzyme labeled reagent and then separated prior to incubation with a chromogenic substrate.

One convenient and rapid technique that has found wide application is the use of a strip generally comprising of solid rod or sheet on which is attached a pad for conducting an immunochemical reaction. The strip can be dipped in a sample solution containing other reagents and subsequently processed to produce a signal based on the amount of analyte in the original sample. Such an immunochemical strip allows for convenient handling, transfers, separations and the like.

It is desirable to develop a new assay technique which provides for accurate detection of an analyte in a sample and which can be conducted without separation and wash steps and with minimal interference from factors in the sample. It is further desirable that the assay be able to be conducted on relatively small quantities of a sample.

2. Brief Description of the Related Art

Patents disclosing a variety of methods involving separation of bound and unbound antigen include U.S. Pat. Nos. Re. 29,169; 3,949,064; 3,984,533; 3,985,867; 4,020,151; 4,039,652; 4,067,959; 4,108,972; 4,145,406; and 4,168,146. A simultaneous calibration heterogenous immunoassay is disclosed in U.S. Pat. No. 4,533,629. Preferential signal production on a surface in immunoassays is described in U.S. Pat. No. 4,299,916. U.S. Pat. No. 4,391,904 discloses test strip kits in immunoassays and compositions therein.

An apparatus for automatic measurement of the test results of agglutination tests is described in U.S. Pat. No. 4,290,997. An apparatus for microscopic examination of specimens is disclosed in U.S. Pat. No. 4,427,634. A measure and funnel is disclosed in U.S. Pat. No. 3,132,768. A biological fluid sample processing apparatus is disclosed in U.S. Pat. No. 3,545,932. U.S. Pat. No. 2,835,246 describes an apparatus for handling medical specimens. A urine testing apparatus is disclosed in U.S. Pat. No. 3,774,455. U.S. Pat. No. 4,473,530 discloses a compact sanitary urine analysis unit.

SUMMARY OF THE INVENTION

We have found that the composition of certain samples containing an analyte affects the result of an assay for the analyte. Sample interference is significant where the assay is performed without separating the sample from the reaction mixture prior to generating a signal related to the amount of analyte in the sample. In effect, without a separation step, the sample interferes by affecting the intensity of the signal so that the signal no longer is related to the amount of analyte in the sample.

In accordance with the present invention, methods and apparatus are provided for determining an analyte in a sample suspected of containing the analyte. The analyte is a member of a specific binding pair (sbp) consisting of ligand and complementary receptor. The method comprises combining in a first aqueous medium (1) the sample, (2) a member of a signal producing system (sps), usually a conjugate of an enzyme and an sbp member, that becomes bound to the surface in relation to the amount of analyte in the sample and (3) a first reagent comprising a non-dispersed surface to which is bound an sbp member. The volume of the first aqueous medium is sufficiently large to allow complete immersion of the first reagent therein and determination of the analyte. The volume of first aqueous medium should not be so large as to result in substantial interference in the determination upon addition of a second reagent reactive with the sps member to generate a signal in relation to the amount of analyte in the sample. The second reagent is present in a second aqueous medium having sufficient volume to substantially increase the volume of the first aqueous medium and thereby further reduce interference in the determination. The second reagent is added to the first aqueous medium without separation of the first reagent therefrom. The first reagent or the medium is examined for the presence of a signal.

An apparatus for performing an assay method in accordance with the invention comprises a vessel having at least one vertical side wall, an open end, and a single closed end generally opposite the open end. The apparatus further comprises a discontinuously narrowed portion adjacent the closed end and defining a well. The apparatus further comprises a ledge depending from the vertical side wall and lying adjacent the narrowed portion. In a preferred embodiment the narrowed portion is formed from a bottom wall and at least one vertical side wall that intersects a wall extending from the vertical side wall of the vessel. The wall extending from the vertical side wall of the vessel constitutes the ledge.

Diagnostic kits for performing the method of the invention are also provided.

DESCRIPTION OF THE SPECIFIC EMBODIMENTS

Figure 1:
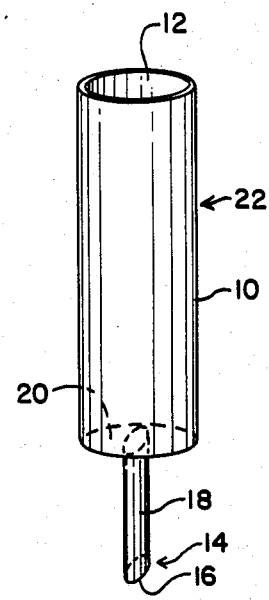

The present invention is concerned with assays for determining an analyte in a sample suspected of containing the analyte where separation steps are minimized or avoided. The general principle on which the present invention is based involves the use of a certain volume of a first liquid medium comprising the sample and an sps member in conjunction with a certain volume of a second liquid medium containing other sps members. The volume of the first liquid medium depends on the sample volume and sps member concentration and is selected so as to allow complete immersion of the first reagent therein and determination of the analyte. This volume is further selected so that substantial interference in the determination from the sample and the sps member can be avoided without separating a first reagent from the liquid medium and washing the first reagent free of sample and sps member. The first reagent comprises a surface to which an sbp member is bound.

As a result of employing a small volume of first aqueous medium and a relatively larger volume of second aqueous medium, separation and washing of the first reagent prior to addition of the second aqueous medium is avoided. The volume of the second aqueous medium should be sufficiently large to substantially increase the volume of the first aqueous medium and thereby dilute the first aqueous medium and substantially reduce interference in the determination from the sample and from the sps member. Usually, the second aqueous medium has a volume that increases the volume of the first aqueous medium by at least three, preferably five, fold.

The present invention resides in the recognition that a small volume of aqueous medium containing the sample and the sps member can be employed in the assay. This small volume of first aqueous medium can be substantially increased by addition of a second aqueous medium so that a substantial reduction in the interference in the determination from the sample is achieved.

Further, the effect of the reaction of unbound sps member with other sps members to generate a signal independent of the signal developed on the first reagent is reduced. The second aqueous medium can be added to the first aqueous medium without separation of the first reagent from the first aqueous medium. The first reagent or the medium can then be examined for the presence of a signal resulting from the signal producting system and related to the amount of analyte in the sample.

An apparatus for carrying out the afore-described method generally has a narrowed portion for containing the volume of the first aqueous medium and allowing the first reagent to be immersed in the first aqueous medium. The apparatus further generally includes a ledge, adjacent to the narrowed portion, on which the first reagent can be placed after addition of the second liquid medium.

The present method has wide application in the field of separation assays, particularly in enzyme immunoassays such as for example enzyme linked immunosorbent assays (ELISA). The invention provides a method which is more convenient and rapid than the conventional approach involving separation and wash steps, particularly where sample interference is a problem.

Before proceeding further with the description of the specific embodiments of the present invention, a number of terms will be defined.

Analyte--the compound or composition to be measured, the material of interest. The analyte can be a member of a specific binding pair (sbp) and may be a ligand, which is mono- or polyvalent, usually antigenic or haptenic, and is a single compound or plurality of compounds which share at least one common epitopic or determinant site.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916, particularly at columns 16 to 23, the disclosure of which is incorporated herein by reference in its entirety.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Label—A member of the signal producing system that is conjugated to an sbp member. The label can be catalysts such as an enzyme, a chromogen such as a fluorescer, dye or chemiluminescer, and so forth.

Labeled sbp member—a label, generally a catalyst, usually an enzyme, conjugated to an sbp member. The labeled sbp member is a member of the signal producing system and the sbp member is chosen to bind to the first reagent in accordance with a particular protocol in an assay.

Signal Producing System—The signal producing system may have one or more components, at least one component being a label or labeled sbp member. The signal producing system generates a signal that relates to the presence or amount of analyte in a sample. The signal producing system includes all of the reagents required to produce a measurable signal. When the label is not conjugated to an sbp member analogous to the analyte, the label is normally bound to an sbp member complementary to an sbp member that is analogous to the analyte. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by use of electromagnetic radiation, desirably by visual examination. For the most part, the signal producing system will involve a chromophoric substrate and enzyme, where chromophoric substrates are enzymatically converted to dyes which absorb light in the ultraviolet or visible region, phosphors, fluorescers or chemiluminescers.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

First reagent—a surface to which is attached an sbp member. The surface will be non-dispersed and have an available surface area of at least about 50 $\mu m^2$ and generally greater, often at least about 1 $mm^2$, usually being on a support, particularly when less than about 0.5 $cm^2$, and can be of any material which is insoluble in water and provides the necessary properties for binding an sbp member and desirably a detectable signal generating compound to provide a desired signal level. Desirably, the surface will be gelatinous, permeable, bibulous, porous or have a rough or irregular structure, which may include channels or indentations, generally having a substantial void volume as compared to total volume. Depending upon the nature of the detectable signal generating compound, the surface will be adsorbent or non-adsorbent, preferably being weakly or non-adsorbent. The surface may be transparent or opaque, a single material or a plurality of materials, mixtures or laminates. A wide variety of materials and shapes may be employed. The surface will be capable of substantially retaining its integrity under the conditions of the assay, so that substances which are bound to the surface will remain bound to the surface and not diffuse into solution. The materials forming the surface are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The surface can be polyfunctional or be capable of being polyfunctionalized to permit covalent bonding of sbp members as well as to permit bonding of other compounds which form a part of the signal producing system.

Binding of sbp members to the surface may be accomplished by well-known techniques, commonly available in the literature. See, for example, "Immobilized Enzymes," Ichiro Chibata, Halsted Press, New York (1978) and Cuatrecasas, J. Bio. Chem., 245:3059 (1970).

Support—The support for the bibulous material where a support is desired or necessary will normally be water insoluble, non-porous, and rigid and will be at least the same length and width as the surface but can be larger. A wide variety of organic and inorganic materials, both natural and synthetic, and combinations thereof, may be employed provided only that the support does not interfere with the surface, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

Immunoreactive strip—A support to which is attached the first reagent. A reference reagent may also be attached. It will frequently be convenient for the immunoreactive strip to be elongated, usually rectangular, with the reagent(s) attached to one end.

Second reagent—one or more members of the signal producing system, which upon reaction with the label generate a detectable signal. The second reagent will usually be an enzyme substrate, but may be a catalyst, an enzyme, coenzyme, chromogenic substrate, or the like, or a combination thereof.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

As mentioned above, the method of the present invention is directed to an assay for determining an analyte in a sample suspected of containing the analyte. The analyte is an sbp member. The method comprises combining in a first aqueous medium (1) the sample, (2) an sps member that becomes bound to the surface in relation to the amount of analyte in the sample and (3) a first reagent. A second reagent and a second aqueous medium is added to the first aqueous medium without separation of the first reagent from the first aqueous medium. The volume of the first aqueous medium is sufficiently large to allow complete immersion of the first reagent therein. The first aqueous medium should contain a sufficient amount of the sample and the sps member to make an accurate determination of the presence or amount of analyte in the sample. As one can appreciate, the amount of sample and of the sps member contribute to the total volume of the first aqueous medium. The total volume of the first aqueous medium including the sample and the sps member must not be so large to result in interference in the determination of the analyte upon addition of the second liquid medium containing the second reagent. The volume of the second aqueous medium should be sufficient to increase the volume of the first aqueous medium by at least 3-, preferably at least 5-, more preferably at least 10-fold, and thereby reduce interference in the determination from the sample and the sps member that have not become bound to the first reagent (unbound sps member). While less dilution may be possible, frequently with less dilution, the sample can affect the accuracy of the analyte determination due to non-specific interference by components of the sample or unbound sps member can react with the second reagent and interfere with production of the signal.

In conventional separation assays the sample and unbound sps member are usually removed by separating the first reagent from the liquid medium, washing the first reagent free of unbound sps member, and contacting the first reagent with the medium containing the second reagent. However, the method and apparatus of the present invention avoid this separation and wash step. Even in assays in accordance with U.S. Pat. Nos. 4,299,916 and 4,391,904 where a separation need not necessarily be performed, certain samples such as body fluids, e.g., milk, blood, urine, serum, etc., cause substantial interference in the signal production when a separation step is omitted. The present method overcomes this problem.

Following the combination of the first and second liquid medium, the first reagent is examined for the presence of a signal. The nature of the signal indicates the presence or amount of analyte in the sample.

In carrying out the assay an aqueous medium will be employed for both the first and second liquid medium. Other polar solvents may also be included, usually oxygenated organic solvents of from 1-6, more usually from 1-4 carbon atoms, including alcohols, ethers and the like. Usually these cosolvents will be present in less than about 40 weight percent, more usually in less than about 20 weight percent.

The pH for the medium will usually be in the range of about 4-11, more usually in the range of about 5-10, and preferably in the range of about 6.4-9.5. The pH is chosen so as to maintain a significant level of specific binding by the receptor while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the assay. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique, and the concentration of the analyte of interest will normally determine the concentration of the other reagents.

While the concentrations of the various reagents will generally be determined by the concentration range of interest of the analyte, the final concentration of each of the reagents will normally be determined empirically to optimize the sensitivity of the assay over the range of interest in accordance with the principle of the present invention. The total binding sites of the members of the specific binding pair which are reciprocal to the analyte will be not less than about 0.1 times the minimum concentration of interest based on binding sites of the analyte and not more than about 10,000 times the maximum concentration of interest based on analyte binding sites, usually about 0.1–1000 times, more usually about 0.3–10 times, the maximum concentration of interest. For ligand analyte, where labelled ligand is employed, the concentration range of the labelled ligand based on equivalents will generally be not less than about $10^{-6}$, more usually not less than $10^{-2}$ times the minimum concentration of interest and not greater than 100, usually not greater than 10, times the maximum concentration of interest. The concentration range of the various sps members is determined by the nature of the analyte, the concentration range of the analyte, the assay, and the sensitivity of the determination.

The volume of the first aqueous medium should be sufficient to allow the first reagent to be immersed therein. Therefore, the volume of the first aqueous medium will depend on the size and shape of the support for first reagent where a support is used, and upon the amount of sample and sps member needed for the determination. The volume of sample will depend on the concentration of analyte and of interfering factors in the sample and on the nature of the sample. As a matter of convenience, the volume of the sample will be from about 1 $\mu$l to 500 $\mu$l, usually 20 to 200 $\mu$l, but may be greater or less than those amounts.

As mentioned above, the surface of the first reagent can be in the form of a pad, a bead, particles, and the like. The surface can be attached to a support; for example, where the surface is a pad, the pad can be attached to a support in the form of an immunoreactive strip, rod, film, etc.

For the most part, the volume of the first aqueous medium is determined on the basis of convenience, cost of the reagents and availability of sample. For purposes of illustration and not limitation, certain exemplary parameters for surfaces that are pads on immunoreactive strips are set forth below. The surface area of the pad can vary between 0.05 to 4 $cm^2$, preferably between 0.1 to 1 $cm^2$ and its volume may vary between 0.001 and 1.0 $cm^3$, preferably 0.005 to 0.2 $cm^3$. The volume of the first aqueous medium must be sufficient to completely wet the pad and may be affected by whether or not the pad is attached to a support and the nature of the container. The immunoreactive strip may have a right angle bend where the pad is situated on a horizontal part of the strip to facilitate immersion in a small volume, or, where the pad is attached on a vertical strip, the volume of first aqueous medium required to immerse the pad can be reduced by employing a container having a narrowed portion. Such a container can be an apparatus of this invention or other apparatus having a narrowed portion for receiving the pad.

More than one pad can be present on an immunoreactive strip. Thus, for example, one can employ both a measurement pad and a calibration pad on a strip in accordance with the teaching of U.S. Pat. No. 4,533,629, the disclosure of which is incorporated herein by reference in its entirety. The measurement and calibration pads will usually be in close juxtaposition on the immunoreactive strip. Accordingly, the volume of the first aqueous medium should be sufficient to immerse all of the pads on the immunoreactive strip in the medium. In addition, more than one set of two pads, i.e. measurement and calibration, can be employed, involving either or both a plurality of measurement surfaces and a plurality of calibration surfaces. For example, a plurality of analytes can be simultaneously determined and/or a plurality of calibration surfaces to provide for a more quantitative result or a different calibration surface associated with each of the measurement surfaces for the different analytes. The volume of the first liquid medium will, therefore, vary depending on the number of pads on the immunoreactive strip; all of the pads should be completely immersed in the first liquid medium.

The dimensions of the support, e.g., immunoreactive strip, are chosen in accordance with the principle of the present invention. The strip must be wide enough to accommodate the pad but narrow enough to be easily received in the narrowed portion of a container in accordance with the present invention. Normally, the surfaces are placed at one end of the strip to facilitate ease of immersion of the pads in the first aqueous medium.

After the sample, first reagent, and sps member have been combined in the first aqueous medium, the medium can be left to stand or can be agitated, preferably left to stand. An incubation period can be involved, generally varying between about 0.5 min. to 1 hour, more usually about 2 min to 30 min.

Next, without separation or transfer of the first reagent, a second reagent is added to the first aqueous medium preceded by, simultaneous with, or subsequent to addition of a second aqueous medium, the volume of which is sufficient to increase the volume of the first aqueous medium by at least 3-, preferably at least 5-, more preferably at least 10-fold, and thereby reduce interference in the determination of the analyte from the sample. The maximum amount of the second liquid medium is not so critical and is usually determined by such factors as expense of reagents, total volume of the reaction vessel, convenience, and the like.

As explained above, the interference in the determination results from the sample and the unbound sps member, which remain in the first aqueous medium and give rise to specific and non-specific interference. Therefore, the volume of the second aqueous medium must be sufficient to reduce such interference to a level where meaningful assay results can be obtained without separation or transfer. We have found that this interference can be substantially reduced by dilution of the aqueous medium while still obtaining an accurate and sensitive determination. Thus, the volume of the second liquid medium is dependent on the volume of the first liquid medium and in some respects to the concentration of unbound analyte and sps members in the first liquid medium. For concentrations of analytes referred to above, the volume of the second liquid medium should be about from 3 to 20 times, preferably about from 8 to 12 times, the volume of the first liquid medium.

After addition of the second liquid medium, the combined medium can be agitated to assist in diffusion of components in the medium. Agitation can be accomplished manually or mechanically. Generally, where a strip is involved, the strip can be moved about within the medium to facilitate mixing of the components.

Another incubation period can be employed with a duration such as described above. The apparatus for carrying out the above determination can possess a ledge, on which the end of the strip having attached surfaces can be placed for ease of viewing. The ledge will be below the level of the liquid medium so that all surfaces remain immersed therein.

Next, the first reagent is examined for the presence of a signal. Frequently, the reagent will be removed from the medium and the surface or surfaces will be blotted with a suitable porous material prior to examination to assist in removal of liquid from the surface. The presence or intensity of the signal is related to the amount of analyte in the sample.

Normally, the signal will be by observation of electromagnetic radiation, particularly ultraviolet or visible light, either absorption or emission, particularly absorption, or electrical properties of the surface. Desirably, light will be in the range from about 250 to 880 nm, usually from about 350 to 700 nm. Visual inspection, reflectometers, fluorometers, spectrophotometers or the like may be employed, depending upon the signal generating compound and the nature of the surface, that is, whether opaque or transparent. Usually, it will be the intensity (transmission or emission) of the signal generator on the surface which will be correlated with the amount of analyte.

The temperature at which the signal is observed will generally range from about 0° to 50° C., more usually from about 15° to 40° C.

Standard samples can be prepared which have known amounts of analyte. The observed signal for each of the standard samples may then be plotted or compared visually, so as to relate concentration to signal. Alternatively, a number of surfaces may be prepared relating to various concentrations, and visual or spectroscopic comparison made between the surface of the sample and the standards. Depending upon the accuracy required, the standards may be made as a prior color chart or may be made by the analyst determining the sample. Once a standard curve has been established, an observed signal may be directly related to the concentration of the analyte.

Methods for calibration of the measurement surface are disclosed in U.S. Pat. No. 4,299,916 at column 15, the disclosure of which is incorporated herein by reference. A preferred calibration technique is disclosed in U.S. Pat. No. 4,533,629.

An apparatus for conducting a determination on an immunoreactive strip in accordance with the present invention comprises a vessel, usually optically transparent, having an open end, and a closed end generally opposite the open end. A narrowed portion is adjacent the closed end and defines a well of a shape suitable to accept the immunoreactive strip. A ledge is outside of and adjacent to the narrowed portion and is capable of preventing the strip from entering the well when the strip is allowed to rest on the ledge. The apparatus is tubular and can be cylindrical, rectangular, oval, or other shape compatible with the principle of the present invention.

In one preferred embodiment the narrowed portion is discontinuously narrowed and formed from a bottom wall and at least one vertical side wall which intersects a wall extending inwardly (ledge) from the vertical side wall of the vessel. The term "discontinuously narrowed" refers to a narrowing such that the dimensions of a horizontal plane of the unnarrowed portion of the vessel are not continued anywhere in the narrowed portion.

In another preferred embodiment, the apparatus is rectangular and includes a narrowed rectangular portion, one side wall of which is an extension of one side wall of the vessel. The ledge comprises a wall extending at an angle from a side wall of the vessel opposite the above side wall. The ledge intersects a side wall of the narrowed portion. The angle of the ledge must not be so great as to allow the strip to enter the well when the strip is allowed to rest on the ledge.

Apparatus in accordance with the present invention are depicted in FIGS. 1-4. The apparatus are tubular by way of example and not limitation. Referring to FIG. 1, the apparatus comprises side wall 10, open end 12, and closed end 14. Closed end 14 has bottom wall 16 and side wall 18. Closed end 14 is narrowed by virtue of wall 20 extending inwardly from side wall 10 to intersect side wall 18. The dimensions of the apparatus will be determined by the dimensions of the immunoreactive strip and by the volume of aqueous media.

Figure 2:
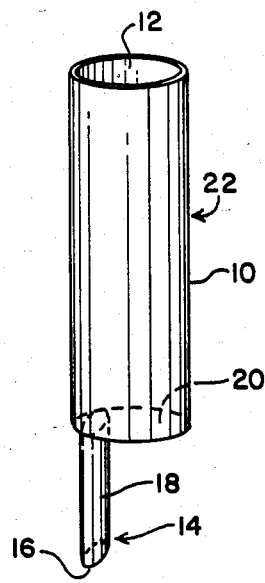

The apparatus in FIG. 2 is similar to that of FIG. 1 except that the narrowed portion is displaced from the vertical axis of top portion 22 and is, therefore, not immediately opposite to the open end.

Figure 3A:
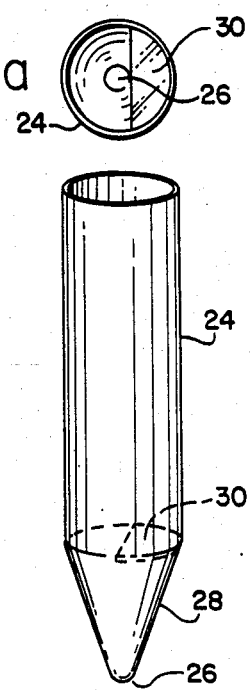
Figure 3B:
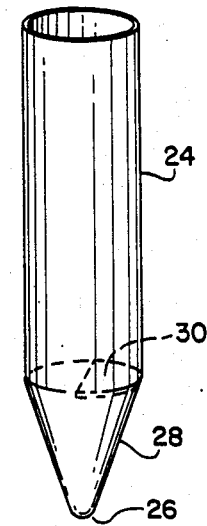

FIGS. 3A and 3B depict an apparatus that is generally cylindrical having side wall 24 and bottom wall 26. Walls 24 and 26 are connected by slanting wall 28. Ledge 30 can project perpendicularly or non-perpendicularly from side wall 24.

Figure 4:
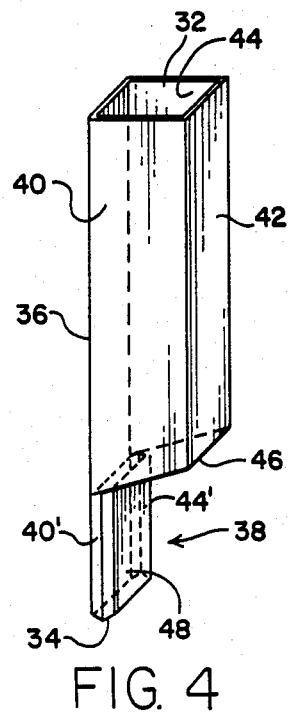

FIG. 4 depicts an apparatus that is rectangular and comprises open end 32 and closed end 34. The apparatus has side wall 36 that is common with narrowed portion 38. The apparatus further comprises walls 40, 42, and 44 and ledge 46. Ledge 46 intersects wall 48 of narrowed portion 38. Walls 40' and 44' of narrowed portion 38 are extensions of walls 40 and 44.

A specific embodiment of the method of the present invention will next be described by way of illustration and not limitation. The sample is a sample of milk having a volume of about 250 μl. The analytes for determination are two β-lactam antibiotics, namely, penicillin and cephalosporin. The first reagent is a strip of about 10 cm in length, about 0.7 cm in width, and about 0.01 cm in thickness. The strip is white opaque polystyrene. Four filter paper pads are located at one end of the strip, two on each side. Each set of two pads is for measurement and calibration in accordance with the teaching of U.S. Pat. No. 4,533,629. The pads are rectangular with dimensions of about 6×7 mm and are about 0.4 mm thick. The pads are spaced about 5 mm apart on a strip. The measurement pads have bound thereto a first conjugate of the antibiotic and glucose oxidase, particularly penicillin-glucose oxidase and cephalosporin-glucose oxidase. Glucose oxidase, as glucose oxidase amine, is bound to each of the measurement and calibration pads. The calibration pads further have bound thereto antibody for a second enzyme, namely, antibody for horse radish peroxidase. The sps member added to the first aqueous medium is a conjugate of an antibody for the antibiotic and the second enzyme, i.e., a conjugate of horse radish peroxidase and antibody for penicillin or cephalosporin. Prior to combining with the sample, the total volume of the aqueous medium is about 0.25 ml. The concentration of the anti-cephalosporin conjugate is 3.5 μg/ml and the concentration of the anti-penicillin conjugate is 3 μg/ml.

The medium containing the sample and the sps members is placed in an apparatus as depicted in FIG. 4. The apparatus has a 1 cm×1.5 cm rectangular unnarrowed portion, 8 cm in length, and a 1 cm×0.3 cm rectangular narrowed portion, 2.5 cm in length.

Figure 5:
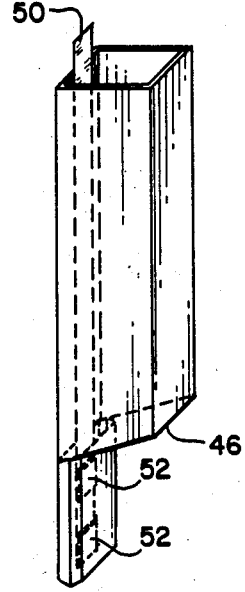

Next, strip 50 containing pads 52 is placed in the apparatus so that the pads are immersed in the liquid medium in the narrowed portion (see FIG. 5). The medium is agitated for 5 seconds by shaking the strip gently. The medium and pads are incubated for a period of from about 3 to 15 minutes.

Next, a substrate solution, the second aqueous medium, containing the remaining sps members is added to the apparatus. The medium contains substrate for glucose oxidase, i.e., glucose, and the chromogenic substrate, 4-chloro-1-naphthol. The volume of the second aqueous medium is about 5 ml. The concentration of glucose in the medium is about 9 mg/ml and of 4-chloro-1-naphthol, from about 0.5 to 1 mg/ml.

Figure 6:
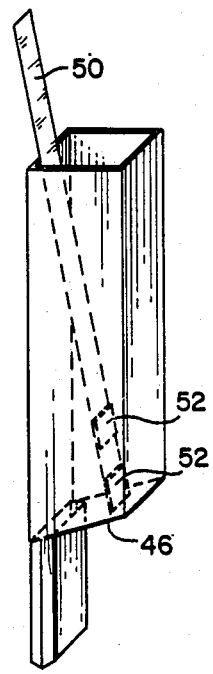

The medium is then agitated by moving the strip up and down in the medium. Preferably, the strip is placed on ledge 46 after agitation (see FIG. 6). After a period of from about 5 to 15 minutes, the strip is removed from the medium and blotted, and the relative color intensities of the measurement and calibration pads are measured. The presence of analyte is indicated by a lighter color on the measurement pad than on the calibration pad.

The invention further includes kits for performing an assay for the determination of an analyte in accordance with the present invention. The kit comprises in packaged combination (a) an apparatus comprising (1) a vessel having an open end and a closed end generally opposite said open end, (2) a narrowed portion adjacent said closed end and defining a well, and (3) a ledge outside of and adjacent to said narrowed portion, (b) a first reagent attached to an immunoreactive strip comprising a surface to which is bound a sbp member, (c) a member of a signal producing system (sps) and (d) a second reagent reactive with said sps member. The amounts of the reagents and the dimensions of the apparatus will be in accordance with the above-described embodiments of the present invention. Other sps members and ancillary reagents can also be included.

The invention has been described in detail with particular reference to the above embodiments. It will be understood, however, that variations and modifications can be effected within the spirit and scope of the invention.

What is claimed is:

1. A method for determining an analyte in a sample suspected of containing said analyte, which analyte is a member of a specific binding pair (sbp) consisting of ligand and complementary receptor, said method comprising providing in combination in a first aqueous medium (1) said sample, (2) a first reagent comprising a non-dispersed surface to which is bound an sbp member and (3) a conjugate of an enzyme and an sbp member that becomes bound to said surface in relation to the amount of analyte in said sample, the volume of said aqueous medium being sufficiently large to allow complete immersion of said first reagent therein;

incubating for a time period sufficient to permit said binding to occur;

adding to said first aqueous medium, without separation of said first reagent therefrom, (1) a second reagent reactive with said conjugate and capable of generating a signal in relation to the amount of analyte in said sample, and (2) a second aqueous medium of sufficient volume to increase the volume of said first aqueous medium by at least three fold, and examining said first reagent for the presence of said signal.

2. The method of claim 1 wherein said second reagent and said second aqueous medium are added simultaneously.

3. The method of claim 1 wherein said volume of first aqueous medium is contained by a narrowed portion of a container.

4. The method of claim 3 wherein said container further comprises means for maintaining said first reagent separate from said narrowed portion.

5. The method of claim 4 wherein said means comprises a ledge adjacent one end of said narrowed portion.

6. The method of claim 5 wherein said ledge is circumferential.

7. The method of claim 6 wherein said ledge is a circumferential wall extending perpendicularly from said narrowed portion to the unnarrowed portion of said container.

8. The method of claim 1 wherein said analyte is selected from the group consisting of proteins and drugs.

9. The method of claim 1 wherein said sbp members are selected from the group consisting of antigens and antibodies.

10. The method of claim 1 wherein said surface is bound to a support.

11. The method of claim 1 wherein said surface is cellulosic.

12. The method of claim 10 wherein said support further contains a calibration surface adjacent to said surface.

13. The method of claim 1 wherein said sbp member bound to said surface is an analyte analog.

14. The method of claim 1 wherein said sbp member bound to said surface is antibody for analyte.

15. The method of claim 1 wherein said sbp member in said conjugate is an antigen or an antibody for analyte.

16. The method of claim 15 wherein said enzyme is one of two enzymes employed in said signal producing system wherein the product of one enzyme is the substrate for the other.

17. The method of claim 1 wherein said analyte is an antibiotic.

18. The method of claim 1 wherein said analyte is a β-lactam antibiotic.

19. The method of claim 1 wherein the volume of said first aqueous medium is from about 200 to 500 μl.

20. The method of claim 1 wherein the volume of said first aqueous medium is increased at least 10-fold by addition of said second aqueous medium.

21. The method of claim 1 wherein said analyte is penicillin, a penicillin analog is bound to said surface, said sbp member is antibody for penicillin bound to the enzyme peroxidase, and glucose oxidase is bound to said surface.

22. The method of claim 1 wherein said second reagent comprises an enzyme substrate.

23. The method of claim 1 wherein said analyte is cephalosporin, a cephalosporin analog is bound to said surface, said sbp member is antibody for cephalosporin bound to the enzyme peroxidase, and glucose oxidase is bound to said surface.

* * * * *